US011709592B2

(12) United States Patent
Moore (10) Patent No.: US 11,709,592 B2
(45) Date of Patent: Jul. 25, 2023

(54) HANDSET FOR CONTROLLING A SUPPORT DEVICE OR A MOVABLE SURFACE

(71) Applicant: Eschmann Holdings Limited, Lancing (GB)

(72) Inventor: Colin Moore, Lancing (GB)

(73) Assignee: Steris Solutions Limited, Leicester (GB)

( * ) Notice: Subject to any disclaimer, the term of this patent is extended or adjusted under 35 U.S.C. 154(b) by 372 days.

(21) Appl. No.: 17/044,419

(22) PCT Filed: Apr. 3, 2019

(86) PCT No.: PCT/EP2019/058410
§ 371 (c)(1),
(2) Date: Oct. 1, 2020

(87) PCT Pub. No.: WO2019/193057
PCT Pub. Date: Oct. 10, 2019

(65) Prior Publication Data
US 2021/0026530 A1    Jan. 28, 2021

(30) Foreign Application Priority Data

Apr. 5, 2018 (GB) .................................... 1805648

(51) Int. Cl.
*G06F 3/04883* (2022.01)
*G16H 40/67* (2018.01)
(Continued)

(52) U.S. Cl.
CPC ......... *G06F 3/04883* (2013.01); *A61G 7/015* (2013.01); *A61G 7/018* (2013.01);
(Continued)

(58) Field of Classification Search
CPC ............... G06F 3/04883; G06F 3/0482; G06F 3/04847; G16H 40/67; G16H 40/63; A61G 7/015; A61G 7/018; A61G 13/08
See application file for complete search history.

(56) References Cited

U.S. PATENT DOCUMENTS

2010/0100841 A1* 4/2010 Shin ................... H04M 1/72427
715/764
2011/0140869 A1* 6/2011 Liu ........................ A61G 7/018
340/286.07

(Continued)

FOREIGN PATENT DOCUMENTS

| EP | 3086218 A1 | 10/2016 |
| JP | 54715493 | 3/1971 |
| WO | 2001/72226 A1 | 10/2001 |

OTHER PUBLICATIONS

International Search Report and Written Opinion in related international application No. PCT/EP2019/058410 dated Jun. 6, 2019.

(Continued)

*Primary Examiner* — David E Choi
(74) *Attorney, Agent, or Firm* — Polsinelli, P.C.

(57) ABSTRACT

A handset for controlling a device having a plurality of movable parts defining a support, or a movable surface, the handset having a housing, a touchscreen display on a front face of the housing, the touchscreen display being adapted to display an image representative of a device or surface to be controlled, and a control system within the housing which is connected to the touchscreen display, wherein the control system has an input module which is adapted to receive an input command in the form of a gesture drawn on the touchscreen display, and an output module which is adapted to generate an output control signal, associated with the input command, for transmission to the device or surface.

40 Claims, 7 Drawing Sheets

(51) Int. Cl.
    *G16H 40/63*     (2018.01)
    *A61G 7/015*     (2006.01)
    *A61G 7/018*     (2006.01)
    *A61G 13/08*     (2006.01)
    *G06F 3/0482*     (2013.01)
    *G06F 3/04847*     (2022.01)

(52) U.S. Cl.
    CPC .......... *A61G 13/08* (2013.01); *G06F 3/0482* (2013.01); *G06F 3/04847* (2013.01); *G16H 40/63* (2018.01); *G16H 40/67* (2018.01); *A61G 2203/12* (2013.01); *G06F 2203/04803* (2013.01)

(56) References Cited

U.S. PATENT DOCUMENTS

| | | | | |
|---|---|---|---|---|
| 2013/0159940 A1* | 6/2013 | Duffy | ............... | G06F 3/017 715/863 |
| 2013/0227433 A1* | 8/2013 | Doray | ............... | G06F 3/0481 715/753 |
| 2014/0189551 A1 | 7/2014 | Kim | | |
| 2014/0250597 A1* | 9/2014 | Chen | ............... | A61G 7/05769 340/12.54 |
| 2014/0277936 A1* | 9/2014 | El Dokor | ............... | B60R 1/072 701/1 |
| 2014/0304917 A1 | 10/2014 | Ruch | | |
| 2015/0135438 A1 | 5/2015 | Marugg | | |
| 2016/0239261 A1* | 8/2016 | Wild | ............... | B60K 37/06 |
| 2016/0250088 A1* | 9/2016 | Williamson | ............... | A61G 7/002 5/617 |
| 2018/0369038 A1 | 12/2018 | Bhimavarapu et al. | | |

OTHER PUBLICATIONS

Combined Search and Examination Report under Sections 17 and 18(3) in related GB application No. 1714138.3 dated Mar. 6, 2018.
Examination Report under 18(3) in related GB application 1714138.3 dated Aug. 6, 2019.
International Preliminary Report on Patentability in related international application No. PCT/2019/058410 dated Oct. 6, 2020.

* cited by examiner

HANDSET FOR CONTROLLING A SUPPORT DEVICE OR A MOVABLE SURFACE

FIELD OF THE INVENTION

The present invention relates to a handset for controlling a device defining a support surface, such as a patient support device, for example a surgical operating table, or a movable surface. The present invention relates to a method for controlling such a support device or movable surface using a handset.

BACKGROUND

Surgical tables, or operating tables, have a variety of different well known configurations, for example comprising a base for standing on a floor, a column extending from the base, and a tabletop providing a patient support surface. There is a general need in the art for surgical tables to have variable height to enable the tabletop to be located at a defined height which is most suitable for the required surgical, therapeutic or diagnostic treatment of a patient positioned on the surgical table. The column is extendable, typically by a telescoping arrangement, to allow the column to be moved between contracted and extended positions in order to lower and/or raise the tabletop to a desired height. In other surgical tables, an arm, instead of a column, can lower and/or raise the tabletop to the desired height.

Still further, the tabletop of the surgical table is generally required to be movable relative to the column or arm so as to be tiltable about two orthogonal horizontal axes, namely a tilt axis extending longitudinally along the length of the tabletop and a trend axis extending transversely across the length of the tabletop.

In addition, the tabletop generally includes a number of independently movable segments. For example a head section, one or more torso sections and one or more leg sections.

It is well known to provide a handset to enable the various movement functions of the surgical operating table to be controlled. The handset may be wirelessly connected to the surgical operating table to be able to send movement commands to the table. Known handsets for controlling surgical operating tables typically comprise many push buttons associated with a variety of icons, and/or text. The icons and text are used to identify the movement available to the respective push button.

The most-used push buttons tend to be located in an array conveniently positioned for manual control. Examples of the most-used push buttons are: HEAD UP, HEAD DOWN, LEG UP, LEG DOWN, BACK UP, BACK DOWN, SLIDE CRANIALLY, SLIDE CAUDALLY, TREND, REVERSE TREND, AUTO LEVEL. Lesser used functions may be available on a display screen, often several menu layers down.

These known handsets suffer from the problem that it can be time consuming and difficult for the healthcare operator to search for and select a push button, from the many push buttons provided, often in a small dimension array, to activate a desired movement of the table. Furthermore, the manual pressing of the selected button to activate the desired movement does not provide any significant visual, audible or touch feedback to the user. In addition, the speed of motion of the selected segment or the table is difficult to control or adjust using the push button. Typically, small adjustments to a selected movement requires the selection of another push button.

The buttons of a handset typically have a fixed usage or movement function because the icon for the respective movement function is printed on, or otherwise physically associated with, the button. Therefore many handsets are bespoke and customised for a respective patient support device. Alternatively, a common handset may be used for plural devices, but some buttons are redundant for the control of at least one of the devices. Icons can be small and difficult to see and interpret, and typically vary between different manufacturers.

Some handsets provide the combination of buttons and a screen. However, the conventional handset for controlling patient support devices are inconvenient because they cannot readily accommodate a large screen in landscape display mode. This is because there are handset size limitations to permit the handset to fit comfortably in the hand, screen size limitations to permit comfortable viewing and use, and aesthetic design problems because a landscape design can appear cumbersome in the hand.

When buttons and a screen are provided in a handset, it may be difficult for a user to find a desired movement function that may be controlled by a button or by a screen input.

There is a need in the art to provide a handset, in particular a handset for controlling a surgical operating table, which has a more ergonomic design than known handsets, and in particular can more easily and/or more controllably enable movement commands to be readily selected for transmission to the device to be controlled.

SUMMARY OF THE INVENTION

The present invention provides a handset for controlling a device having a plurality of movable parts defining a support, or a movable surface, the handset comprising a housing, a touchscreen display on a front face of the housing, the touchscreen display being adapted to display an image representative of a device or surface to be controlled, and a control system within the housing which is connected to the touchscreen display, wherein the control system comprises an input module which is adapted to receive an input command in the form of a gesture drawn on the touchscreen display, and an output module which is adapted to generate an output control signal, associated with the input command, for transmission to the device or surface.

In some embodiments of the present invention, the control system is adapted to generate an output control signal for transmission to the device or surface associated with an input command in the form of a gesture, wherein the gesture is in the form of a line, a shape or an alphanumeric character, drawn on the touchscreen display. Typically, the gesture is a line, but may alternatively be any shape or alphanumeric character, or any series of connected lines. Most preferably, the gesture is a single line, of any shape or orientation, drawn in a single swipe over the touchscreen surface.

The embodiments of the present invention may control any movable surface or any device having a plurality of movable elements. In preferred embodiments, the device is a patient support device, for example a seat, bed or surgical operating table. The present invention further provides a surgical operating table in combination with the handset of the present invention.

The present invention further provides a method of controlling a device having a plurality of movable parts defining a support, or controlling a movable surface, using a handset, the method comprising the steps of:

i. inputting an input command in the form of a gesture drawn on a touchscreen display of the handset to select a desired movement function of a movable part of the device or of the movable surface; and ii. generating an output control signal for transmission from the handset to the device or the movable surface, the output control signal being associated with the input command.

Again, the gesture may be in the form of a line, a shape or an alphanumeric character, drawn on the touchscreen display. Typically, the gesture is a line, but may alternatively be any shape or alphanumeric character.

In this specification, the term "touchscreen display" is used in a broad sense to mean any device presenting the image of a screen with displayed images, and optionally icons, which are touch sensitive. The touchscreen display may comprise a single unitary touchscreen device with displayed images and icons on a unitary screen and the touchscreen being touch sensitive so that pressing of the touchscreen in the vicinity of the images or icons activates a signal associated with the image or icon. Alternatively, the touchscreen display may comprise an array of plural individual displayed images or icons, each of which is associated with a respective switch device located beneath the respective image or icon.

Although the preferred embodiments relate to a handset configured to control a surgical operating table, the handset may be employed, or configured to be employed, to control the movement of any movable or adjustable surface, for example of a patient support device.

Fundamentally, the preferred embodiments of the present invention provide an image of a view of a patient support device to be controlled. This is typically a level (i.e. typically horizontal) view of a surface of the patient support device or of the patient support device. The view may be a side view and/or an end view. In use, the user draws a gesture, e.g. a line, on the touchscreen display which is representative of the position for the patient support device or at least one movable element of the patient support device. For example, the line represents a change in the position and/or orientation of the element or device.

The drawn gesture line provides positional information for the requested movement function to the software/hardware in the handset. The software/hardware, which may be in the handset or in the device to be controlled, interprets the drawn gesture. The software/hardware analyses the drawn gesture line and matches the shape and location of the line to an available physical movement of the element or device. The software/hardware provides one or more control elements to be displayed or highlighted, the control elements being associated with movements corresponding to the interpretation of the drawn gesture. Operation of the one or more control elements generates a command to reposition the element or device or surface.

The accuracy of the drawn gesture line to achieve a desired movement may be within a broad tolerance, since the length, location, shape and/or orientation of the drawn gesture line may be interpreted by the software/hardware within tolerance bands to interpret the intended movement function from the drawn gesture line which is not required to be geometrically accurate. For example there may be a +/−10 degree tolerance for a drawn gesture line that is intended to be horizontal and aligned with an image of the element or device. For example there may be a +/−5 mm tolerance for a drawn gesture line that is intended to extend outside a control zone or be above or below an image of the element or device.

If the drawn gesture line is not recognised or does not conform to an input tolerance then the operation is deemed a failure and the user is informed and asked to retry. Some drawn gesture lines for specific movement or control functions may be drawn anywhere on the touchscreen.

The preferred embodiments provide a two-action input requirement for achieving a particular selected movement function. First, the drawn gesture line is inputted to select a particular movement function. Subsequently, the touchscreen displays control buttons for the user to generate and transmit a signal to produce the selected physical movement. The requirement for two successive user actions before a physical movement can be implemented provides a safety feature to avoid inadvertent or accidental physical movements of the patient support device.

The software/hardware may be configured to recognise a drawn gesture line which may correspond to a pre-set shape length, location, shape and/or orientation of a line stored in a memory to enable a respective predetermined orientation of the patient support device to be efficiently achieved.

The handset of the preferred embodiments provides a number of advantages over known handsets.

In the preferred embodiments of the present invention, the handset, which is preferably configured to be in the form of a tablet, has a large touchscreen user interface. Gesture control provides access to all movements of the patient support device without the need to search for, or understand the meaning of, icons on physical buttons. The touchscreen can be configured to large buttons and information for easy reading. The gesture control also can provide access to other menu items and functions. The gesture controlled touchscreen can readily be updated with a software update to incorporate new movements of the patient support device and the control of new accessories for the patient support device. The gesture controlled touchscreen can be aligned to present a display and controls which are readily selected or modified or dedicated to the specific patient support device to be controlled.

The handset can provide haptic and visual feedback to the user when selected.

The touchscreen surface is easy to clean, which is important in a sterile environment of an operating theatre.

The handset can be safely controlled by a user in a surgical or other medical environment. A desired movement function is selected by inputting a drawn gesture line on the touchscreen. The drawn gesture line is highlighted to confirm its position, shape and orientation. After the line has been drawn, control elements, for example in the form of buttons, are presented and a desired control element is pressed or otherwise engaged to cause a function to initiate the desired direction and speed of movement to achieve the desired movement and final configuration of the patient support device or surface to be controlled. Release of the control element terminates movement. Here, the term "control element" is used broadly to include any control element, such as a push button, area to be pressed, lever, joystick, slider, etc. which can be manually engaged to control the device as described above.

The ergonomic design of the preferred embodiments is convenient for left-handed or right-handed use, and can be used in a single-handed operation. The tablet shape enables the handset readily to be placed securely and stably on a surface.

BRIEF DESCRIPTION OF THE DRAWINGS

Embodiments of the present invention will now be described by way of example only with reference to the accompanying drawings, in which.

DETAILED DESCRIPTION

Figure 1:
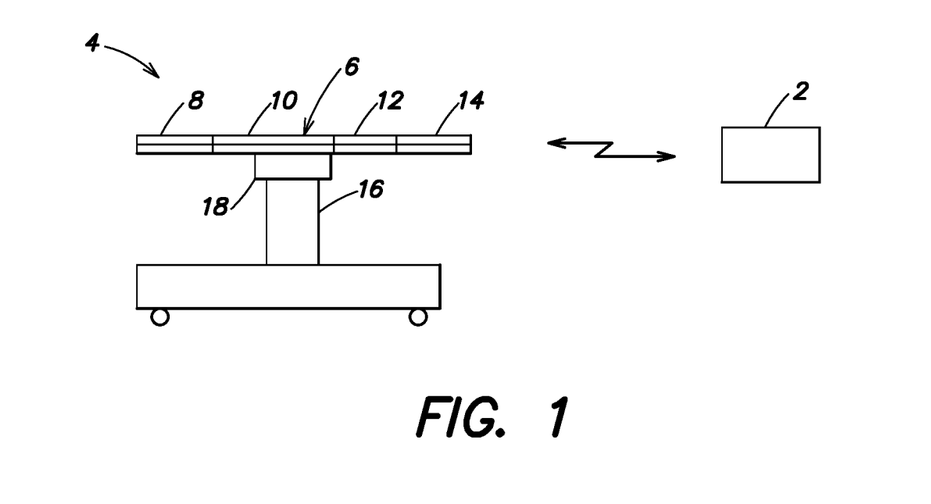
FIG. 1 is a schematic view of a handset according to an embodiment of the present invention in combination with a surgical operating table to be controlled by the handset.
Figure 2:
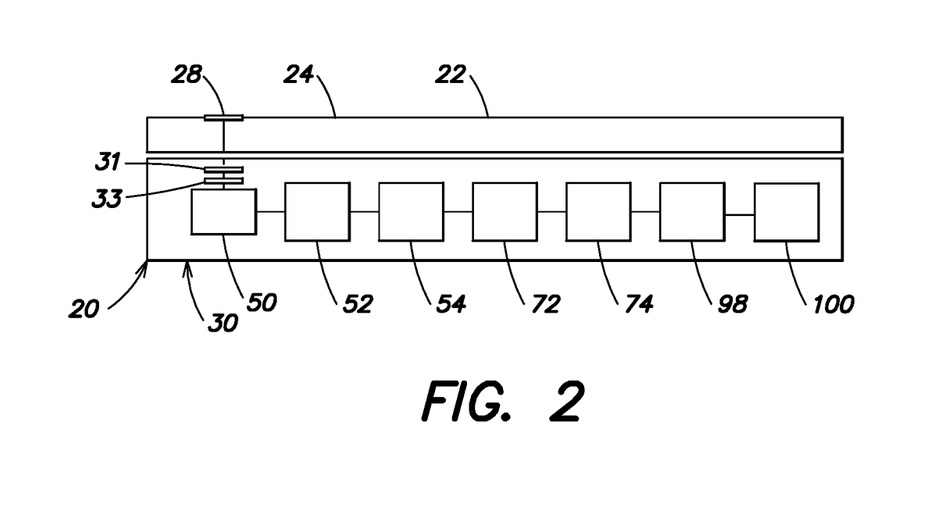
FIG. 2 is a schematic side view of a control system in the handset of FIG. 1.

Referring to FIGS. 1 and 2, there is shown a handset 2 according to an embodiment of the present invention. The handset 2 is configured for controlling a device having a plurality of movable elements or parts, in particular a surgical operating table 4. However the handset 2 may be configured or used to control other patient support devices having a plurality of movable elements, for example, beds, chairs, etc.

The surgical operating table 4 has movable parts, in the form of movable elements, which comprise segments of a tabletop 6 of the surgical operating table 4. These segments comprise a head section 8, an upper body section 10, a lower body section 12 and one or two leg sections 14 (some persons skilled in the art of surgical operating tables may alternatively call these segments a head section 8, a back section 10, a seat section 12 and one or two leg sections 14). The movable elements also comprise a column 16, or other height control device, on which the tabletop 6 is mounted. A mechanism, generally indicated by reference numeral 18, is provided in the surgical operating table 4 which can be controlled to incline the tabletop 6 in a Trendelenburg position, the entire tabletop 6 being inclined so that the head section 8 is lowered relative to the other sections of the tabletop 6, and a Reverse Trendelenburg position, the entire tabletop 6 being inclined so that the head section 8 is raised relative to the other sections of the tabletop 6, by rotating the tabletop 6 about a transverse trend axis extending across the tabletop 6. The mechanism 18 also can be controlled to tilt the tabletop 6 by rotating the tabletop 6 about a longitudinal tilt axis extending along the tabletop 6. The column 16 can be controlled by being extended or retracted to raise or lower the tabletop 6.

Drive mechanisms are provided within the surgical operating table 4 to move the tabletop 6 to a desired position or configuration according to a command from the handset 2. Typically, the handset 2 is adapted to control the surgical operating table 4 by wireless communication. The handset 2 is adapted translationally and/or rotationally to move individual segments of the tabletop 6 or the entire tabletop 6.

Thus, individual segments of the tabletop 6 or the entire tabletop 6 can be translationally or rotationally moved in a vertical orientation, i.e. in an upward direction or a downward direction; the entire tabletop 6 can be translationally moved in a lateral horizontal orientation, i.e. in a direction extending from the head section 8 to the one or two leg sections 14 or in an opposite direction; and/or the entire tabletop 6 can be rotationally moved about the transverse trend axis and/or the longitudinal tilt axis.

The handset 2 comprises a housing 20. A touchscreen display 22 is located on a front face 24 of the housing 20. The housing 2 and touchscreen display 22 have the shape and configuration of a tablet computer. The housing may be provided with one or more handles 26 and is typically ergonomically configured to provide right-handed or left-handed manual operation by a user. Typically, two handles 26 are provided on opposite sides of the handset 2. A strap may be fitted to the handles 26 for fitting the handset 2 around the arm of a user or suspending the handset 2 around the neck of a user. The handset 2 further comprises at least one physical switch 28 on the front face 24, for example an on/off switch 28.

The handset 2 further comprises a control system 30 within the housing 20 which is connected to the touchscreen display 22 and at least one physical switch 28. The control system 30 is arranged to generate an output control signal for transmission to the device, in the illustrated embodiment the device being the surgical operating table 4, associated with an input command at the touchscreen display 22 in the form of a gesture drawn as a line on the touchscreen display 22.

FIG. 2 shows, in a highly schematic form, the control circuitry within the handset. In FIG. 2, the control system 30 is shown as comprising a plurality of hardware components. In embodiments of the present invention, these hardware components may each individually or collectively be embodied in hardware or software or a combination of both hardware and software, as will be immediately apparent to those skilled in the art.

Figure 3:
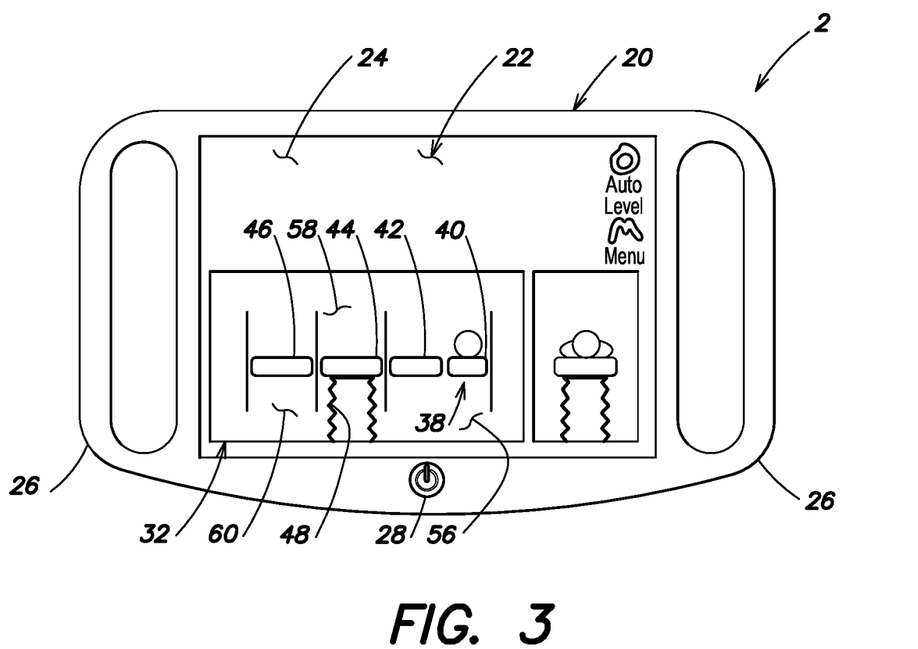
FIG. 3 is a schematic plan view of a handset of FIG. 1 in a first example of an operating mode.

The control system 30 comprises an input module 31 which is adapted to receive an input command in the form of a gesture drawn on the touchscreen display 22 and an output module 54 which is adapted to generate an output control signal, associated with the input command, for transmission to the device or surface to be controlled. The control system 30 further comprises a control module 33 which is adapted, in response to the input command, to display, or to enable the function of, a user-operable control element, as described hereinbelow for control elements 66, 68, 70 with reference to the "Control Movement" screen 36. The output module 54 is adapted, in response to operation of the user-operable control element(s) 66, 68, 70, to generate the output control signal which is associated with the input command. FIG. 3 shows a schematic illustrative screenshot of a "Home" screen 32 on the touchscreen display 22 prior to input of an input command at the touchscreen display 22 in the form of a gesture.

Figure 4:
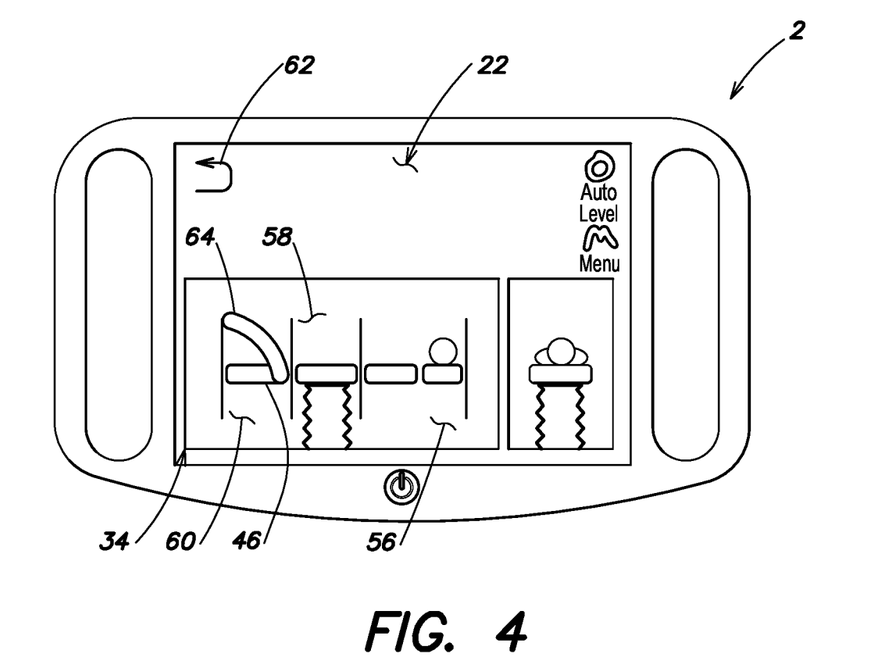
FIG. 4 is a schematic plan view of a handset of FIG. 1 in a second example of an operating mode.

FIG. 4 shows a schematic illustrative screenshot of a "Select Movement Function" screen 34 on the touchscreen display 22 during input of an input command at the touchscreen display 22 in the form of a gesture.

Figure 5:
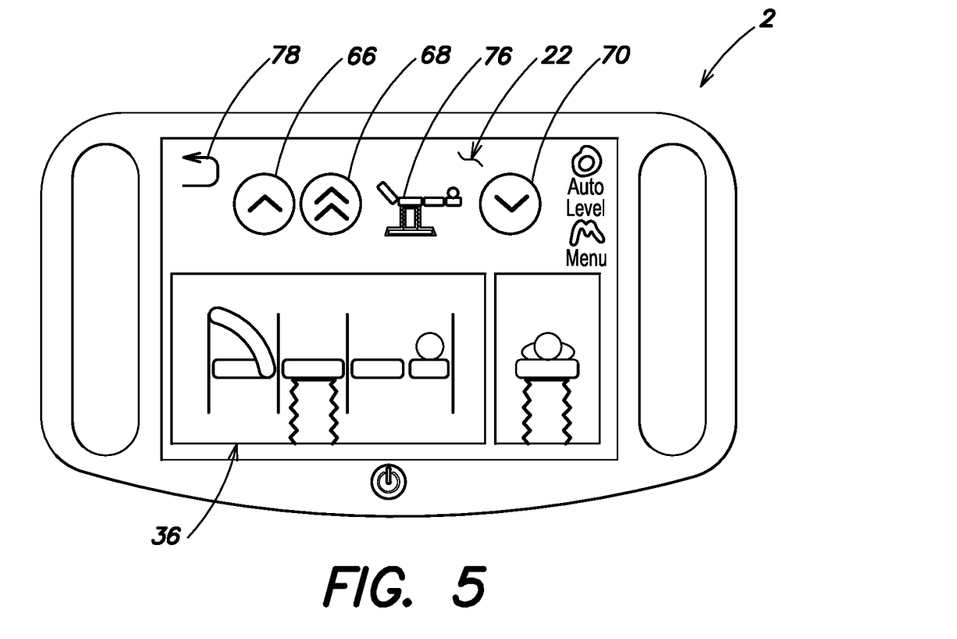
FIG. 5 is a schematic plan view of a handset of FIG. 1 in a third example of an operating mode.

FIG. 5 shows a schematic illustrative screenshot of a "Control Movement" screen 36 on the touchscreen display 22 after input of an input command at the touchscreen display 22 in the form of a gesture.

Referring to these Figures, the "Home" or "Draw a New Position" screen 32 displays an image 38 representative of the patient support device to be controlled. The image 38 shows elements, for example movable elements, of the surgical operating table to be controlled, in particular the segments of a tabletop 6, which comprise a head section image 40, an upper body section image 42, a lower body section image 44 and the image 46 of one or two leg sections. The image 38 also shows a column image 48 beneath the lower body section image 44 (although there may be one or more body section images and the column may be associated with any selected body section image). The image 38 may either be static or movable to correlate with a selected movement function, and correspondingly the individual elements of the image 38 that make up the image of the device or surface to be controlled, for example the head section image 40, upper body section image 42, lower body section image 44 and the image 46 of one or two leg sections, may individually be static or movable to correlate with a selected movement function.

The control system 30 is adapted to generate the output control signal for transmission to the device 4 associated with an input command in the form of a gesture drawn as a line on the touchscreen display 22.

The control system 30 can detect the initiation and termination of the drawn gesture, and after gesture has been drawn the control system 30 can process the information in the gesture. It does not matter which end of the line is drawn first; it is the final gesture shape and position that determine what control signal will ultimately be provided to the device or surface to be controlled. In the preferred embodiments, the gesture is a continuously drawn gesture, e.g. line, even when it is a special shape such as "chair", because the line shape is determined when the drawing device, which may be a finger or stylus, or other device, is in contact with the screen.

The control system 30 comprises a characteristic determiner 50 which is adapted to determine a characteristic of the line drawn on the touchscreen display 22. An analyser 52 is adapted to analyse the determined characteristic against a feature of the displayed image and to generate an analysis signal. Typically, the determined characteristic is at least one of the length, location, shape and orientation of the line, or a combination of any two or more thereof. The output module 54 is adapted to generate the output control signal associated with the analysis signal. As discussed above, these components may each individually or collectively be embodied in hardware or software or a combination of both hardware and software, as will be immediately apparent to those skilled in the art.

The analyser 52 is adapted to analyse the determined characteristic against at least one of the length, location, shape and orientation of the displayed image to generate the analysis signal. For example, the analyser 52 is adapted to determine whether the line drawn on the touchscreen display 22 is substantially inclined to or substantially aligned with the image representative of the patient support device to be controlled thereby respectively to generate an analysis signal. The analysis signal is utilized by the output module 54 to generate the output control signal.

Preferably, the output control signal is configured to raise or lower one of the movable elements of the patient support device to be controlled or to rotate the patient support device to be controlled. The output control signal may be configured to raise, lower or laterally move the patient support device to be controlled. As explained further hereinbelow, multiple movements can happen together in one smooth movement, for example if the user selects to AutoLevel the table by pressing an AutoLevel button on the screen, or by drawing a circle anywhere on the screen; and Autolevel can also include a change in HEIGHT.

In preferred embodiments, the analyser 52 is adapted to determine that the line drawn on the touchscreen display 22 is substantially inclined to the image representative of a patient support device to be controlled when the line is inclined at an angle of greater than 10 degrees to the image and/or the analyser 52 is adapted to determine that the line drawn on the touchscreen display 22 is substantially aligned with the image representative of a patient support device to be controlled when the line is inclined at an angle of no more than 10 degrees to the image. However, other angle thresholds to distinguish between an inclined line and an aligned (or level or horizontal) line may be employed.

In the preferred embodiments, as shown in FIG. 3, the touchscreen display 22 is adapted to be divided into a plurality of first control zones 56, 58, 60. Each first control zone 56, 58, 60 corresponds to a respective at least one element of the image. Thus first control zones 56, 58, 60 respectively correspond to the head section image 40 and the upper body section image 42, lower body section image 44 and leg image 46.

The analyser 52 is adapted to determine whether the line drawn on the touchscreen display is within a single first control zone 56, 58, 60 or extends across two or more first control zones 56, 58, 60 to determine a zonal characteristic of the line. The analyser 52 is adapted to analyse the determined zonal characteristic against a feature of the displayed image to generate the analysis signal. The output module 54 is adapted to utilize the analysis signal to generate the output control signal so that the zonal characteristic determines whether one or all of the plurality of movable elements of the entire patient support device to be controlled are moved.

A number of different movement functions can be selected using the input gesture on the touchscreen display 22 when the touchscreen display 22 displays the image 38 representative of the patient support device, and the gesture line is drawn in the vicinity or at least partly over the image.

FIG. 4 shows a schematic illustrative screenshot of a "Select Movement Function" screen 34 on the touchscreen display 22 during input of an input command at the touchscreen display 22 in the form of a gesture. The Select Movement Function" screen 34 may, as shown in FIG. 4, simply be the "Home" or "Draw a New Position" screen 32, actively and dynamically additionally showing the input command as the gesture is being drawn.

Referring to FIG. 4, an inclined line 64 has been drawn manually by finger touch, or by using an implement, above the leg image 46. This constitutes an inputting of an input command in the form of a gesture drawn as a line on a touchscreen display 22 of the handset 2 to select a desired movement function of a movable leg section 14 of the surgical operating table 4. The analyser 52 determines whether the line 64 drawn on the touchscreen display 22 is within a single first control zone 56, 58, 60 or extends across two or more first control zones 56, 58, 60 to determine a zonal characteristic of the line 64. In this example, the line 64 has been drawn in only zone 60, so the zonal characteristic is that the line 64 has been drawn in a single zone 60.

A return icon 62 shown on the touchscreen display 22 permits the user to return to the Home screen or "Draw a New Position" screen 32, for example in the event of an incorrect input or gesture. Additionally, the handset 2 may be configured to return to the Home screen 32 after a timeout period, if the user has not initiated a gesture input within a pre-set default time period.

The analyser 52 analyses the determined zonal characteristic against a feature of the displayed image to generate the analysis signal. The output control signal is generated associated with the analysis signal so that the zonal characteristic determines whether one or all of the plurality of movable elements of the entire patient support device are moved.

In particular, when the analyser 52 determines that the line 64 drawn on the touchscreen display 22 is within a single first control zone 56, 58, 60, the output control signal controls only the respective at least one movable element of the patient support device which corresponds to the at least one element of the image of the respective first control zone. In this example, since the line has been drawn in only zone 60, only the corresponding element, namely leg section 14, is subsequently controlled.

In FIG. 4, the line 64 is within a single first control zone 60 and is substantially inclined to the at least one element of the image, which is leg image 46, of the respective first control zone 60. This causes the output control signal to change the inclination or height of the respective leg section 14 of which corresponds to the at least one element of the leg image 46 of the respective first control zone 60.

Since in FIG. 4, the line 64 drawn on the touchscreen display 22 is within a single first control zone 60 and is substantially inclined to, and above, the leg image 46. Therefore the output control signal raises the respective leg section 14. In contrast, if the line 64 drawn on the touchscreen display 22 is within a single first control zone 60 and is substantially inclined to, and below, the leg image 46, the output control signal lowers the respective leg section 14.

After the line has been drawn, which inputs an input command at the touchscreen display 22 in the form of a gesture, as shown in FIG. 5 a "Control Movement" screen 36 is shown on the touchscreen display 22.

In the "Control Movement" screen 36, the touchscreen display 22 displays a plurality of control elements 66, 68, 70, in this embodiment in the form of buttons 66, 68, 70. As described above, the term "control element" is used broadly to include any control element, such as a push button, area to be pressed, lever, joystick, slider, etc. which can be manually engaged or otherwise operated to control the device as described above, although the illustrated embodiment uses buttons 66, 68, 70.

The touchscreen display 22 is, in the illustrated embodiment, adapted to a display a plurality of the control elements 66, 68, 70, preferably after the input module 31 has received the input command. Typically, the touchscreen display 22 is adapted to display a selected type of one or more control elements 66, 68, 70, the type being selected to be associated with the input command received by the input module 31. In alternative embodiments, the control elements could comprise physical switches that are enabled by the input command received by the input module 31, or comprise elements displayed on the touchscreen display but only enabled by the input command received by the input module 31.

In the illustrated embodiment, the input command at the touchscreen display 22, in the form of a gesture, causes one or more control elements 66, 68, 70 to be displayed on the touchscreen display 22. Alternatively, one or more control elements 66, 68, 70 may be displayed on the touchscreen display 22 during the inputting of the input command, i.e. during drawing of the gesture, and are enabled to function as a result of the inputting of the input command. In either case, one or more control elements 66, 68, 70 are thereby selected to be able, when subsequently operated, to permit or cause an output control signal, associated with the input command, to be transmitted to the device or surface to be controlled.

The control system 30 is thereby configured to transmit the output control signal in response to operation of at least one of the control buttons 66, 68, 70. The control system 30 comprises a speed controller 72 which is adapted to include a speed command in the output control signal, and at least one of the control buttons 66, 68, 70 is configured to provide a speed input to the speed controller 72. The control system 30 also comprises a direction controller 74 which is adapted to include a direction command in the output control signal, and at least one of the control buttons 66, 68, 70 is configured to provide a direction input to the direction controller 74.

In the illustrated embodiment, two control buttons 66, 68 are configured to provide an UP direction input and another control button 70 is configured to provide a DOWN direction input. The control button 66 is configured to provide a speed input corresponding to a first, slow, speed and the control button 68 is configured to provide a speed input corresponding to a second, fast speed. Therefore in this embodiments there are two UP control buttons 66, 68 to provide a slow UP and a fast UP control and one down button 70 to provide a slow DOWN control. However, it will be apparent to the skilled person that other control buttons and associated speed or direction configurations may be employed.

In the example of FIG. 5, the "Control Movement" screen 36 also shows a pictorial illustration 76 of the selected configuration of the device as a result of the selected movement function selected on the preceding "Select Movement Function" screen 34.

In order to transmit the output control signal which has been generated from the output module 54, the desired control button 66, 68, 70 is pressed. This pressing initiates movement of the device to be controlled, and causes the leg section 14 to be moved up or down, and at the desired speed, from its current initial starting position, to the desired inclination. Release of the respective control button 66, 68, 70 terminates the movement of the device to be controlled. Pressing the button 66, 68, 70 does not initiate a movement to a pre-set position, for example to AutoLevel, Chair or Flex. The table only moves whilst the button 66, 68, 70 is held. Releasing the button 66, 68, 70 stops all movement immediately.

After a delay or time-out period, the touchscreen display 22 returns to the "Home" screen 32 automatically. An additional Return or Home button 78 may be provided in the touchscreen display 22 to return the touchscreen display 22 to the "Home" screen 32.

In an alternative example, the leg section 14 may be correspondingly lowered by drawing a downwardly inclined line 64 beneath the leg image 46 in zone 60, and then employing the control buttons 66, 68, 70 to transmit the output control signal to the device.

In an alternative example, the head section 8 and upper body section 10 may be correspondingly raised or lowered by drawing an upwardly or downwardly inclined line above or beneath the head image 40 and upper body image 42 in zone 56, and then employing the control buttons 66, 68, 70 to transmit the output control signal to the device.

When the analysing step determines that the line drawn on the touchscreen display 22 is within a single first control zone 56, 58, 60, or extends across two or more first control zones 56, 58, 60, and is substantially aligned with the at least one element of the image of the respective first control zone 56, 58, 60, the output control signal controls the height of the patient support device.

Figure 6:
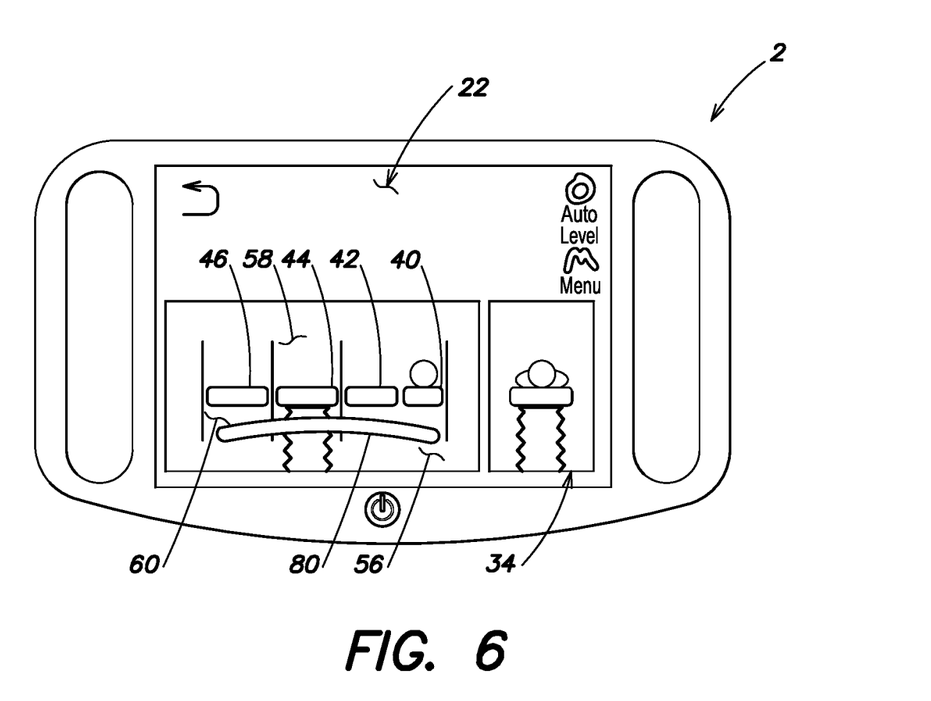
FIG. 6 is a schematic plan view of a handset of FIG. 1 in a fourth example of an operating mode.

For example, as shown in FIG. 6 which shows a "Select Movement Function" screen 34, the line 80 is drawn in zone 56 beneath the head image 40, upper body image 42, lower body image 44 and leg image 46. When the line 80 is at least 5 mm, as measured on the touchscreen 22, below the head image 40, upper body image 42, lower body image 44 and leg image 46 and the line 80 is substantially aligned with the head image 40, upper body image 42, lower body image 44 and leg image 46 since the line 80 is inclined at an angle of no more than 10 degrees to the images, the output control signal is configured to lower the height of the patient support device, in this example, the tabletop of the surgical operating table 4, e.g. by lowering the column.

However, other distance thresholds to distinguish between an aligned (or level or horizontal) line above or below the image may be employed.

Correspondingly, a line drawn above, and aligned with, the head image 40, upper body image 42, lower body image 44 and leg image 46 would raise the height of the patient support device.

In alternative embodiments, a line drawn above or below, and aligned with, any other image or combination of images within the first control zones 56, 58, 60, may raise or lower the patient support device. Again, the speed may be controlled by the control buttons 66, 68, 70.

In other alternative movement functions, when the analysing step determines that the line drawn on the touchscreen display extends across two or more first control zones, the output control signal controls the inclination or translational position of the patient support device.

Figure 7:
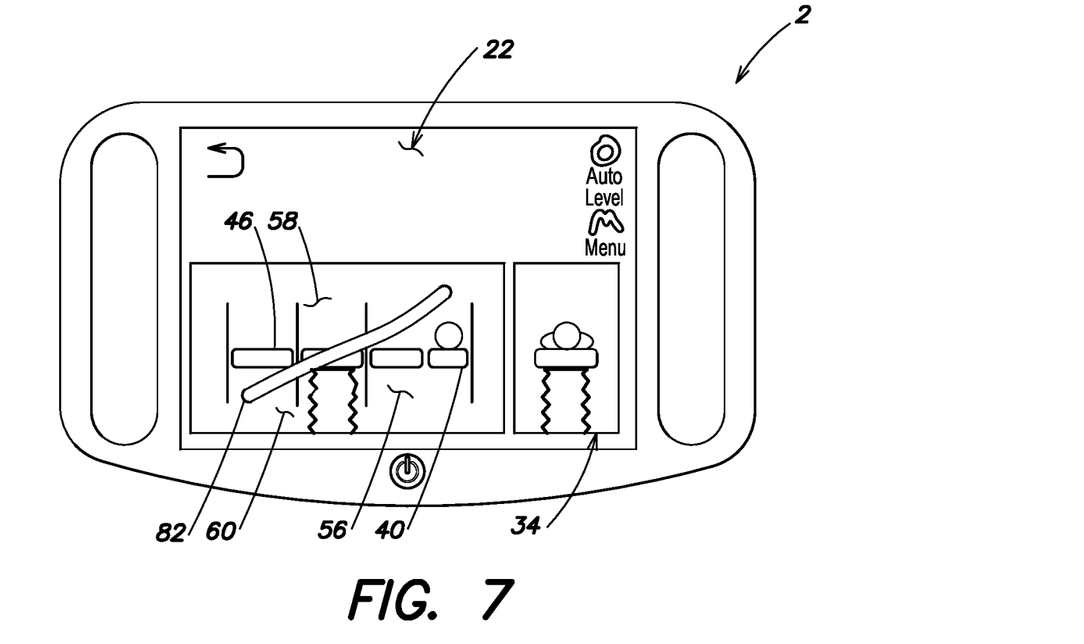
FIG. 7 is a schematic plan view of a handset of FIG. 1 in a fifth example of an operating mode.

Referring to FIG. 7 which shows a "Select Movement Function" screen 34, when the analysing step determines that the line 82 drawn on the touchscreen display 22 extends across two or more first control zones 56, 58, 60 and is substantially inclined at a respective orientation to elements of the image of the respective first control zones, the output control signal rotationally moves the patient support device, in a Trendelenburg or Reverse Trendelenburg motion, at a corresponding respective orientation. In FIG. 7, the line 82 is inclined from a high position above the head section image 40 to a low position below the leg section image 46, and extends across all three first control zones 56, 58, 60. This causes the movement function to be selected as a reverse Trendelenburg movement that is subsequently controlled by the control buttons 66, 68, 70 as described above.

In contrast, if the line is inclined from a high position above the leg section image 46 to a low position below the head section image 40, and extends across two or more first control zones 56, 58, 60, this causes the movement function to be selected as a Trendelenburg movement that is subsequently controlled by the control buttons 66, 68, 70 as described above.

When selecting a reverse Trendelenburg movement or a Trendelenburg movement, the line should extend over two or more first control zones 56, 58, 60 and should be inclined at an angle above a threshold minimum angle, for example 10 degrees, relative to the tabletop in the image.

Figure 8:
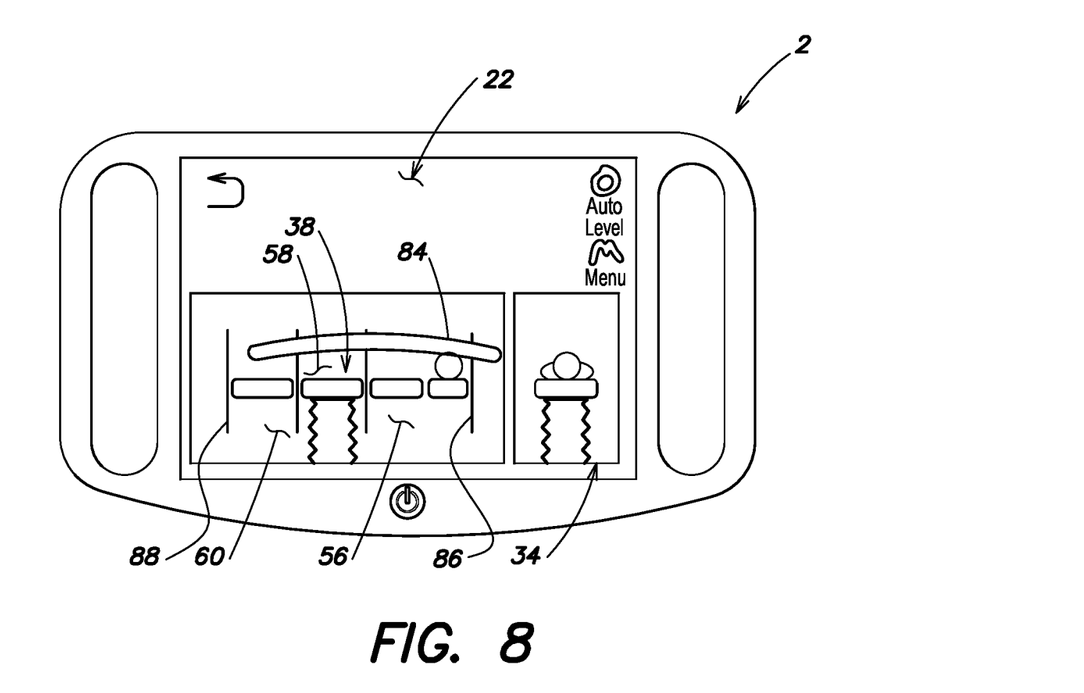
FIG. 8 is a schematic plan view of a handset of FIG. 1 in a sixth example of an operating mode.

Referring to FIG. 8 which shows a "Select Movement Function" screen 34, when the analysing step determines that the line 84 drawn on the touchscreen display 22 extends across two or more first control zones 56, 58, 60, and extends beyond an end 86, 88 of the plurality of first control zones 56, 58, 60, the output control signal moves the patient support device to be controlled using a selected movement function.

For example, the user could just swipe along the drawn tabletop in the direction of SLIDE, within a 0 mm tolerance. The line could fall inside just one section, or two sections, or take in all three sections, and could also break through the end section as well.

For example, when such a line 84 is substantially aligned with at least one element of the image 38, the output control signal laterally translates the patient support device to be controlled, for example by sliding the tabletop relative to the column in a direction toward the end at which the line 84 extended beyond the end 86, 88 of the plurality of first control zones 56, 58, 60.

By selecting which end 86, 88 that the line 84 extends beyond, the slide direction can be readily selected. The line may be required to extend by a predetermined distance, for example at least 5 mm, beyond an end 86, 88 of the plurality of first control zones 56, 58, 60 in order to select the lateral movement function.

Figure 9:
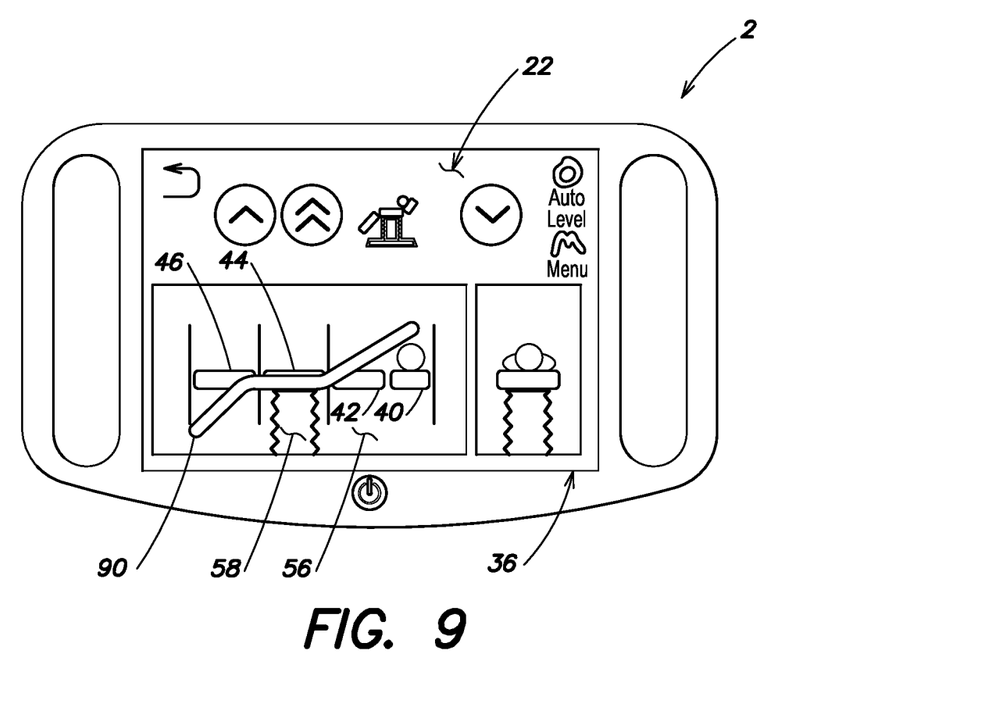
FIG. 9 is a schematic plan view of a handset of FIG. 1 in a seventh example of an operating mode.

Referring to FIG. 9, which shows a "Control Movement" screen 36, when the analysing step determines that the line 90 drawn on the touchscreen display 22 extends across two or more first control zones 56, 58, 60, the output control signal controls the respective movable elements of the patient support device which correspond to the elements of the image of the respective two or more first control zones 56, 58, 60. The output control signal can change the inclination or height of the respective movable element of the patient support device which corresponds to element of the image of the respective first control zone 56, 58, 60.

In the embodiment illustrated, the line 90 has a central aligned portion over the lower body section image 44 and two similarly inclined portions over the leg section image 46 and the upper torso section image 42 and the head section image 40, or in the respective corresponding control zones 56, 58, 60 of these sections. This shaped line 90 resembles the shape of a chair.

The shape is stored as a predetermined shape in a memory and the line 90 can cause the movable elements of the patient support device to be disposed into a pre-set chair position corresponding to or associated with that shape. Other predetermined shapes corresponding to or associated with pre-set positions can similarly be stored in the memory.

Figure 10:
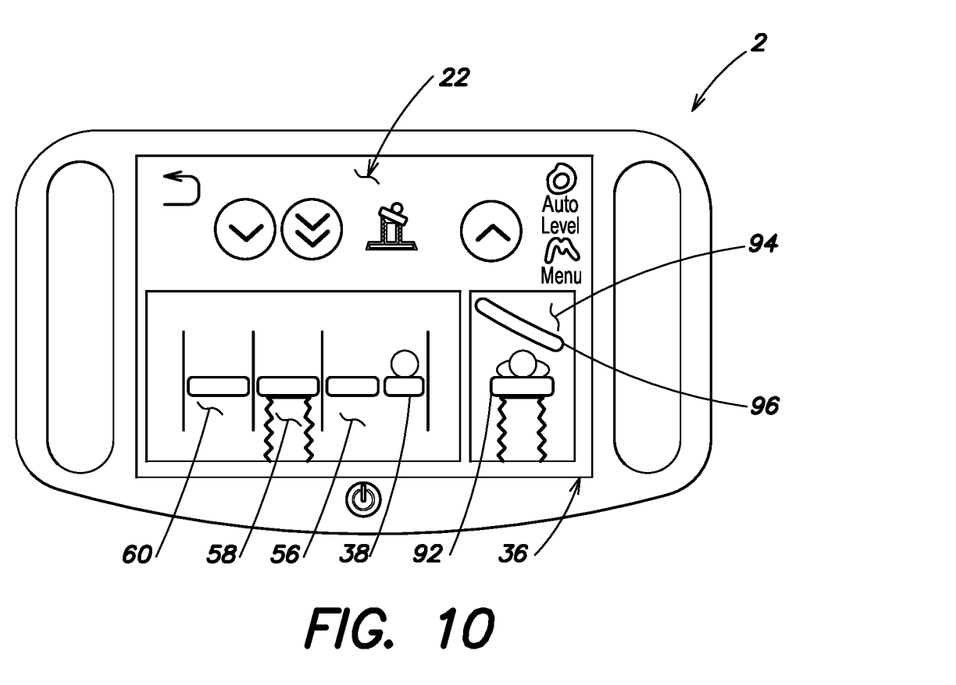
FIG. 10 is a schematic plan view of a handset of FIG. 1 in an eighth example of an operating mode.

As shown in FIG. 10, which shows a "Control Movement" screen 36, in addition to image 38 which shows a side view of the patient support device to be controlled and also the individual sections to be controlled, the touchscreen display 22 is preferably adapted to display a second image 92 of the patient support device to be controlled, which is an end view orthogonal to the side view. A second control zone 94 corresponding to the second image 92 is provided by the touchscreen display 22. The second control zone 94 is provided to enable the entire patient support device to be easily controlled as an alternative to using the first control zones 56, 58, 60.

For example, as shown in FIG. 10, when the analyser 52 determines that the line 96 drawn on the touchscreen display 22 is anywhere within the second control zone 94 and is substantially inclined to the second image 92, the output control signal is configured to rotationally tilt the patient support device to be controlled, for example about a longitudinal axis extending between the ends of the patient support device. The direction of rotation of the rotational tilt corresponds to rotational orientation of the line 96 relative to the second image 92.

Correspondingly, the height of the patient support device can be controlled by drawing a line above or below the second image 92, for respectively raising or lowering the patient support device. The line is preferably aligned with the second image 92.

In alternative examples, the height of the patient support device may alternatively be controlled by drawing a vertical line over the image of the column in either of the first image 38 and the second image 92, and the drawing direction of the line, or the vertical position of the line relative to the image of the column, may be used for respectively raising or lowering the patient support device.

In further alternative examples, the lateral position of the patient support device may alternatively be controlled by drawing an aligned, i.e. substantially horizontal, line over the image of the tabletop in the first image 38, and the drawing direction of the line, or the horizontal position of the line relative to the image of the tabletop, may be used for respectively laterally sliding the tabletop of the patient support device in a direction towards the leg section or toward the head section.

Referring back to FIG. 2, in the illustrated embodiment the control system 30 comprises an input command analyser 98 which is adapted to determine a characteristic of a two-dimensionally shaped line drawn on the touchscreen display 22, to analyse the determined characteristic against a plurality of stored characteristics which are stored in a memory 100, and to generate a selected pre-set signal. In one example, the plurality of stored characteristics includes a first shape corresponding to a menu function and the selected pre-set signal causes a menu to be displayed on the touchscreen display. In other examples the plurality of stored characteristics include a plurality of predetermined shapes corresponding to pre-set positions for the patient support device.

Figure 11:
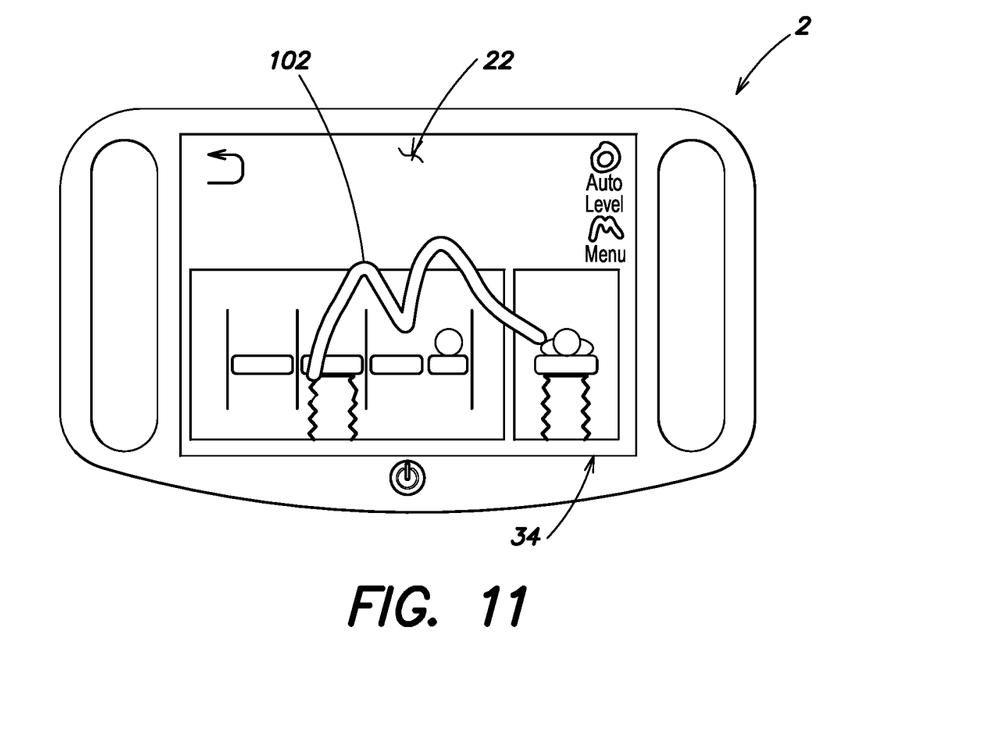
FIG. 11 is a schematic plan view of a handset of FIG. 1 in a ninth example of an operating mode.

As shown in FIG. 11 which shows a "Select Movement Function" screen 34, if a shape 102 resembling a letter M is drawn on the touchscreen display 22, the "Menu" screen may be displayed. Alternatively, if a shape resembling a circle, i.e. O, is drawn on the touchscreen display 22, the selected pre-sect signal causes the output control signal to control an auto-level function of the patient support device to be controlled. The input command analyser 98 may additionally or alternatively be provided to control pre-set positions of the patient support device to be achieved, such as the chair shape described above, when predetermined shapes are drawn on the touchscreen display 22. Of course, other shapes may be provided to select different functions from those described above.

Figure 12:
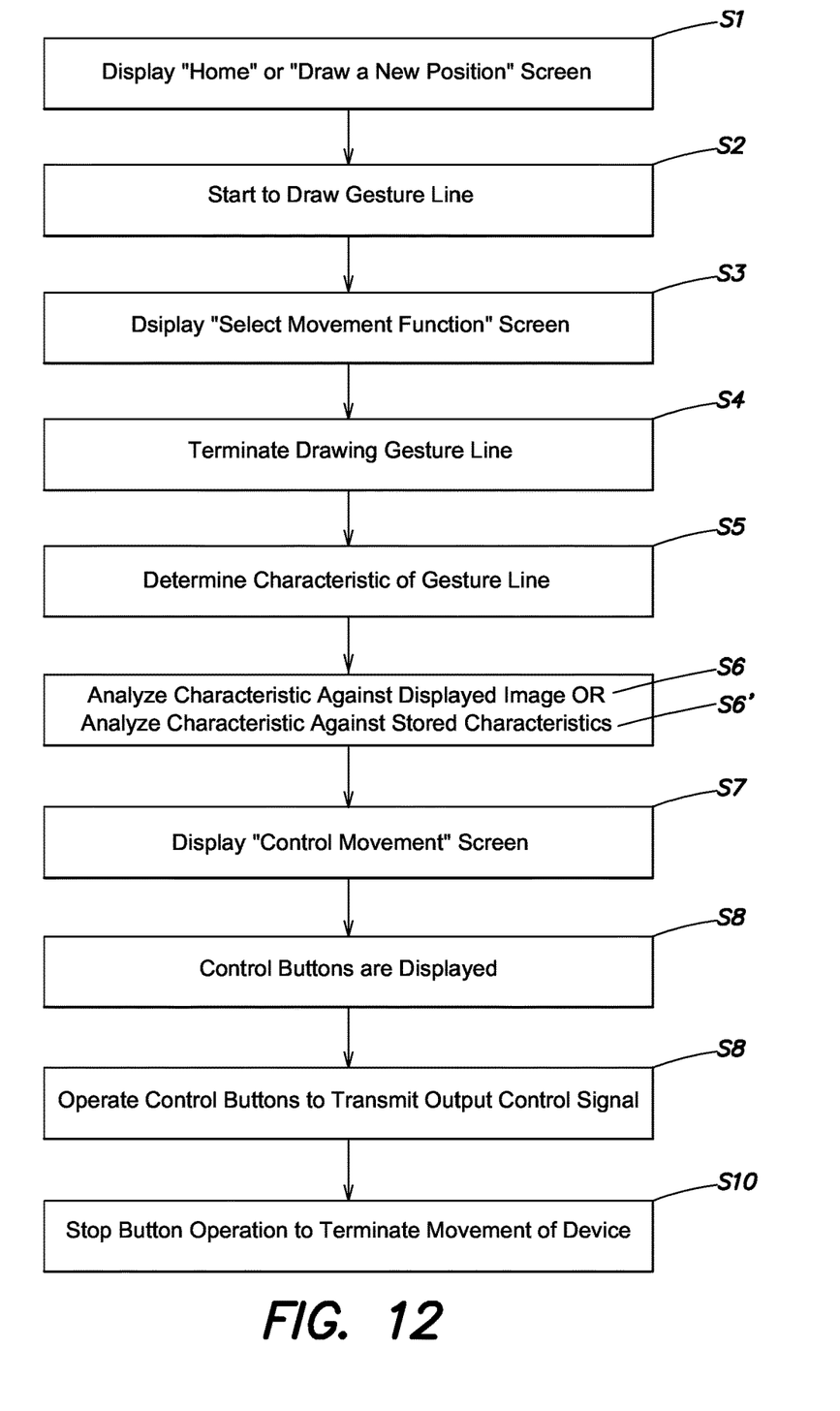
FIG. 12 is a schematic diagram of sequence of steps in a method of controlling a surgical operating table by a handset according to another embodiment of the present invention.

In an embodiment of the method of controlling a patient support device having a plurality of movable elements using a handset, the method has a sequence of steps as described below with reference to FIG. 12.

In a step S1 the "Home" or "Draw a New Position" screen is displayed and the touchscreen display displays an image representative of the patient support device, for example as shown in FIG. 3.

Thereafter, in step S2 an input command in the form of a gesture drawn as a line on a touchscreen display of the handset is inputted to select a desired movement function of a movable element of the patient support device. The gesture line may be drawn in the vicinity or at least partly over the image, or at least in one or more first control zones. Alternatively, for some pre-set shapes, the line may be drawn anywhere on the touchscreen.

After initiation of step S2, in step S3 the "Select Movement Function" screen 34 is displayed on the touchscreen display 22, for example as shown in FIG. 4, during input of an input command at the touchscreen display 22 in the form of a gesture. The "Select Movement Function" screen 34 may be the "Home" screen additionally showing the drawn gesture.

In step S4, the drawing of the gesture line is terminated.

In step S5, a characteristic of the gesture line drawn on the touchscreen display is determined.

In step S6, the determined characteristic is analysed against a feature of the displayed image to generate an analysis signal. Alternatively, dependent upon the determined characteristic, in step S6', the determined characteristic is analysed against a plurality of stored characteristics to generating a selected pre-set signal.

In step S7, after input of the input command at the touchscreen display 22 in the form of a gesture, and the subsequent analysis of the input command, the "Control Movement" screen 36 is displayed on the touchscreen display 22.

In step S8, the appropriate control buttons for the required movement are displayed.

In step S9, one of the control buttons is pressed to control a speed and/or direction of movement, this generating an output control signal which is associated with the analysis signal or selected pre-set signal. This also causes the output control signal to be transmitted, typically wirelessly, from the handset to the patient support device associated with the original input command.

In step S10, the control button is released to terminate transmission of the output control signal and to terminate movement of the patient support device.

Various modifications can be made to the above-described embodiments without departing from the scope of the present invention, which is defined by the claims.

The invention claimed is:

1. A handset for controlling a device having a plurality of movable parts defining a support, or a movable surface, the handset comprising a housing, a touchscreen display on a front face of the housing, the touchscreen display being adapted to display an image representative of a device or surface to be controlled, and a control system within the housing which is connected to the touchscreen display, wherein the control system comprises an input module which is adapted to receive an input command in the form of a gesture drawn on the touchscreen display, and an output module which is adapted to generate an output control signal, associated with the input command, for transmission to the device or surface, wherein the touchscreen display is adapted to display the image in the form of a plurality of parts of the device or surface to be controlled, and the touchscreen display is adapted to be divided into a plurality of first control zones, each control zone corresponding to a respective at least one element of the image, wherein the control system is adapted so that when the analyser determines that the gesture drawn on the touchscreen display is within a single first control zone, the output control signal is configured to control only the respective at least one movable part of the device or surface to be controlled which corresponds to the at least one element of the image of the respective first control zone, and wherein the control system is adapted so that when the analyser determines that the gesture drawn on the touchscreen display is within a single first control zone and is substantially inclined to the at least one element of the image of the respective first control zone, the output control signal is configured to change the inclination or height of the respective at least one movable part of the device or surface to be controlled which corresponds to the at least one element of the image of the respective first control zone.

2. The handset according to claim 1 wherein the input module is adapted to receive an input command in the form of a gesture, wherein the gesture is in the form of a line, a shape or an alphanumeric character, drawn on the touchscreen display.

3. The handset according to claim 1 wherein the control system comprises a characteristic determiner which is adapted to determine a characteristic of the gesture drawn on the touchscreen display, wherein the determined characteristic is at least one of the length, location, shape and orientation of the gesture, or a combination of any two or more thereof; and an analyser which is adapted to analyse the determined characteristic against a feature of the displayed image and to generate an analysis signal, wherein the analyser is adapted to analyse the determined characteristic against at least one of the length, location, shape and orientation of the displayed image to generate the analysis signal; and the output module is adapted to utilize the analysis signal to generate the output control signal.

4. The handset according to claim 3 wherein the analyser is adapted to determine whether the gesture drawn on the touchscreen display is substantially inclined to or substantially aligned with the image representative of a device or surface to be controlled thereby to generate the analysis signal.

5. The handset according to claim 4 wherein the analyser is adapted to determine that the gesture drawn on the touchscreen display is substantially inclined to the image representative of a device or surface to be controlled when the gesture is inclined at an angle of greater than 10 degrees to the image and/or the analyser is adapted to determine that the gesture drawn on the touchscreen display is substantially aligned with the image representative of a device or surface to be controlled when the gesture is inclined at an angle of no more than 10 degrees to the image.

6. The handset according to claim 4 wherein the output control signal is configured to raise or lower one of the movable parts of the device to be controlled, or to raise or lower a part of the movable surface, or to rotate at least one of the movable parts of the device or at least a part of the surface to be controlled, or the output control signal is configured to raise, lower, rotate or laterally move the device or surface to be controlled.

7. The handset according to claim 1 wherein the analyser is adapted to determine whether Originally Filed the gesture drawn on the touchscreen display is within a single first control zone or extends across two or more first control zones to determine a zonal characteristic of the gesture; and the analyser is adapted to analyse the determined zonal characteristic against a feature of the displayed image to generate the analysis signal.

8. The handset according to claim 7 wherein the output module is adapted to generate the output control signal utilizing the analysis signal so that the zonal characteristic determines whether one or all of the plurality of parts of the device or surface to be controlled are moved.

9. The handset according to claim 1 wherein the control system is adapted so that when the analyser determines that the gesture drawn on the touchscreen display is within a single first control zone and is substantially inclined to, and above or below, the at least one element of the image of the respective first control zone, the output control signal is configured to raise or lower, respectively, the respective at least one part of the device or surface to be controlled which corresponds to the at least one element of the image of the respective first control zone.

10. The handset according to claim 1 wherein the touchscreen display is adapted to display a second image of the device or surface to be controlled, and the touchscreen display is adapted to provide a second control zone corresponding to the second image.

11. The handset according to claim 10 wherein the control system is adapted so that when the analyser determines that the gesture drawn on the touchscreen display is within the second control zone and is substantially inclined to the second image, the output control signal is configured to rotationally tilt the device or surface to be controlled.

12. The handset according to claim 10 wherein the direction of rotation of the rotational tilt corresponds to rotational orientation of the gesture relative to the second image.

13. The handset according to claim 10 wherein the control system is adapted so that when the analyser determines that the gesture drawn on the touchscreen display is within the second control zone and is above or below the second image, the output control signal is configured to raise or lower, respectively, the device or surface to be controlled.

14. The handset according to claim 1 wherein the control system further comprises a control module which is adapted, in response to the input command, to display, or to enable the function of, a user-operable control element, and the output module is adapted, in response to operation of the user-operable control element, to generate the output control signal.

15. The handset according to claim 14 wherein the touchscreen display is adapted to a display a plurality of the control elements.

16. The handset according to claim 15 wherein the touchscreen display is adapted to display the plurality of the control elements after the input module has received the input command.

17. The handset according to claim 16 wherein the touchscreen display is adapted to display a selected type of one or more control elements, the type being selected to be associated with the input command received by the input module.

18. The handset according to claim 14 wherein the control system is configured so that release of a control element, which is used to transmit the output control signal, terminates transmission of the output control signal.

19. The handset according to claim 14 wherein the control system comprises a speed controller which is adapted to include a speed command in the output control signal, and wherein at least one of the control elements is configured to provide a speed input to the speed controller.

20. The handset according to claim 19 wherein one control element is configured to provide a speed input corresponding to a first speed and another control element is configured to provide a speed input corresponding to a second speed, wherein the first speed is lower than the second speed.

21. The handset according to claim 14 wherein the control system comprises a direction controller which is adapted to include a direction command in the output control signal, and wherein at least one of the control elements is configured to provide a direction input to the direction controller.

22. The handset according to claim 21 wherein one control element is configured to provide a direction input corresponding to a first direction and another control element is configured to provide a direction input corresponding to a second direction, wherein the first and second directions are opposite.

23. The handset according to claim 1 wherein the device is a patient support device or the surface is a surface of a support device.

24. The handset according to claim 1 which is adapted to control a surgical operation table having a tabletop comprises a plurality of movable elements and a height control device for raising or lowering the tabletop.

25. A handset for controlling a device having a plurality of movable parts defining a support, or a movable surface, the handset comprising a housing, a touchscreen display on a front face of the housing, the touchscreen display being adapted to display an image representative of a device or surface to be controlled, and a control system within the housing which is connected to the touchscreen display, wherein the control system comprises an input module which is adapted to receive an input command in the form of a gesture drawn on the touchscreen display, and an output module which is adapted to generate an output control signal, associated with the input command, for transmission to the device or surface, wherein the touchscreen display is adapted to display the image in the form of a plurality of parts of the device or surface to be controlled, and the touchscreen display is adapted to be divided into a plurality of first control zones, each control zone corresponding to a respective at least one element of the image, wherein the control system is adapted so that when the analyser determines that the gesture drawn on the touchscreen display extends across two or more first control zones, the output control signal is configured to control the inclination or translational position of the device or surface to be controlled.

26. The handset according to claim 25 wherein the control system is adapted so that when the analyser determines that the gesture drawn on the touchscreen display is within two or more first control zones and is substantially aligned with the at least one element of the image of the respective first control zones, the output control signal is configured to control the height of a device or surface to be controlled.

27. The handset according to claim 26 wherein the control system is adapted so that when the analyser determines that the gesture drawn on the touchscreen display is within two or more first control zones and is substantially aligned with, and above or below, the at least one element of the image of the respective first control zones, the output control signal is configured to raise or lower, respectively, the height of the device or surface to be controlled.

28. The handset according to claim 27 wherein the analyser is adapted to determine that the gesture drawn on the touchscreen display is above or below the image representative of a device or surface to be controlled when the gesture is at least 5 mm above or below, respectively, the image.

29. The handset according to claim 25 wherein the control system is adapted so that when the analyser determines that the gesture drawn on the touchscreen extends across two or more first control zones and is substantially inclined at a respective orientation to elements of the image of the respective first control zones, the output control signal is configured to rotationally tilt the device or surface to be controlled at a corresponding respective orientation.

30. The handset according to claim 25 wherein the control system is adapted so that when the analyser determines that the gesture drawn on the touchscreen display extends across two or more first control zones, the output control signal is configured to control the respective movable parts of the device or surface to be controlled which correspond to the elements of the image of the respective two or more first control zones.

31. The handset according to claim 25 wherein the control system is adapted so that when the analyser determines that the gesture drawn on the touchscreen display extends across two or more first control zones, and extends beyond an end of the plurality of first control zones, the output control signal is configured to move the device or surface to be controlled.

32. The handset according to claim 31 wherein the control system is adapted so that when the analyser determines that the gesture drawn on the touchscreen display extends across two or more first control zones, and extends beyond an end of the plurality of first control zones, and is substantially aligned with at least one element of the image, the output control signal is configured laterally to translate the device or surface to be controlled.

33. The handset according to claim 31 wherein the analyser is adapted to determine that the gesture drawn on the touchscreen display extends beyond an end of the plurality of first control zones when the gesture extends by a distance of at least 5 mm beyond an end of the plurality of first control zones.

34. The handset according to claim 31 wherein the control system is adapted so that when the analyser determines that the gesture drawn on the touchscreen display extends beyond an end of the plurality of first control zones, the output control signal is configured to move the device or surface to be controlled in a direction corresponding to the location, relative to the end, of an extending part of the gesture drawn on the touchscreen display.

35. The handset according to claim 25 wherein the device is a patient support device or the surface is a surface of a patient support device.

36. The handset according to claim 25 which is adapted to control a surgical operation table having a tabletop comprises a plurality of movable elements and a height control device for raising or lowering the tabletop.

37. A handset for controlling a device having a plurality of movable parts defining a support, or a movable surface, the handset comprising a housing, a touchscreen display on a front face of the housing, the touchscreen display being adapted to display an image representative of a device or surface to be controlled, and a control system within the housing which is connected to the touchscreen display, wherein the control system comprises an input module which is adapted to receive an input command in the form of a gesture drawn on the touchscreen display, and an output module which is adapted to generate an output control signal, associated with the input command, for transmission to the device or surface, wherein the control system comprises an input command analyser which is adapted to determine a characteristic of a two-dimensionally shaped gesture drawn on the touchscreen display, to analyse the determined characteristic against a plurality of stored characteristics, and to generate a selected pre-set signal, wherein the plurality of stored characteristics includes a first shape corresponding to an auto-level function, and the selected pre-set signal causes the output control signal to control an auto-level function of the device or surface to be controlled.

38. The handset according to claim 37 wherein the plurality of stored characteristics includes a second shape corresponding to a menu function and the selected pre-set signal causes a menu or home display to be displayed on the touchscreen display.

39. The handset according to claim 37 wherein the device is a patient support device or the surface is a surface of a patient support device.

40. The handset according to claim 37 which is adapted to control a surgical operation table having a tabletop comprises a plurality of movable elements and a height control device for raising or lowering the tabletop.

* * * * *